US010098539B2

(12) United States Patent
Konofagou et al.

(10) Patent No.: US 10,098,539 B2
(45) Date of Patent: Oct. 16, 2018

(54) SYSTEMS AND METHODS FOR NON-INVASIVE BRAIN STIMULATION WITH ULTRASOUND

(71) Applicant: THE TRUSTEES OF COLUMBIA UNIVERSITY IN THE CITY OF NEW YORK, New York, NY (US)

(72) Inventors: Elisa E. Konofagou, New York, NY (US); Hermes Arytto Salles Kamimura, Ribeirao Preto (BR)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 60 days.

(21) Appl. No.: 15/040,926

(22) Filed: Feb. 10, 2016

(65) Prior Publication Data
US 2016/0242648 A1 Aug. 25, 2016

Related U.S. Application Data

(60) Provisional application No. 62/114,321, filed on Feb. 10, 2015.

(51) Int. Cl.
A61B 3/11 (2006.01)
A61B 5/11 (2006.01)
(Continued)

(52) U.S. Cl.
CPC .......... *A61B 3/113* (2013.01); *A61B 3/11* (2013.01); *A61B 5/1128* (2013.01);
(Continued)

(58) Field of Classification Search
CPC ..... A61M 37/00; A61M 37/0092; A61N 7/00; A61B 17/225; A61B 8/0808; A61B 5/0071; A61B 8/481; A61B 5/055
(Continued)

(56) References Cited

U.S. PATENT DOCUMENTS 7,699,768 B2  4/2010  Kishawi et al.
8,206,299 B2  6/2012  Foley et al.
(Continued)

FOREIGN PATENT DOCUMENTS

WO  WO 2014/127091 A1  8/2014
WO  WO 2014/160964 A1  10/2014

OTHER PUBLICATIONS

International Search Report dated Sep. 27, 2017 in International Application No. PCT/US2017/044200.
(Continued)

*Primary Examiner* — Carl H Layno
*Assistant Examiner* — Jon Eric C Morales
(74) *Attorney, Agent, or Firm* — Baker Botts L.L.P.

(57) ABSTRACT

Systems and methods for non-invasive brain stimulation using focused ultrasound are provided. An exemplary method of non-invasive brain stimulation in the brain of a subject can include securing the subject in a fixed position relative to an ultrasound source and providing a focused ultrasound having one or more ultrasound parameters to a location in the brain of the subject, the location and the one or more ultrasound parameters selected to evoke a physical response of the subject, and measuring the physical response of the subject.

42 Claims, 10 Drawing Sheets

(51) Int. Cl.
*A61B 3/113* (2006.01)
*A61N 7/02* (2006.01)
*A61B 5/00* (2006.01)
*A61B 5/0205* (2006.01)
*A61N 7/00* (2006.01)

(52) U.S. Cl.
CPC ............. *A61B 5/4848* (2013.01); *A61N 7/02* (2013.01); *A61B 5/0077* (2013.01); *A61B 5/0205* (2013.01); *A61B 5/4821* (2013.01); *A61N 2007/0026* (2013.01)

(58) Field of Classification Search
USPC ................................................. 601/2; 604/22
See application file for complete search history.

(56) References Cited

U.S. PATENT DOCUMENTS

| | | |
|---|---|---|
| 2007/0088345 A1 | 4/2007 | Larson et al. |
| 2009/0005711 A1* | 1/2009 | Konofagou .......... A61B 8/0816 601/2 |
| 2009/0112133 A1 | 4/2009 | Deisseroth et al. |
| 2010/0087728 A1 | 4/2010 | Jarvik et al. |
| 2010/0318002 A1 | 12/2010 | Prus et al. |
| 2011/0112394 A1 | 5/2011 | Mishelevich |
| 2012/0065479 A1 | 3/2012 | Lahiji et al. |
| 2012/0197163 A1* | 8/2012 | Mishelevich ............ A61N 7/00 601/2 |
| 2012/0289869 A1 | 11/2012 | Tyler |
| 2013/0046229 A1* | 2/2013 | Konofagou .......... A61B 17/225 604/22 |
| 2013/0245505 A1 | 9/2013 | Khuri-Yakub et al. |
| 2013/0331905 A1 | 12/2013 | Haessler |
| 2014/0094682 A1 | 4/2014 | Foley et al. |
| 2014/0264660 A1 | 9/2014 | Rothberg et al. |
| 2015/0065871 A1 | 3/2015 | Konofagou et al. |
| 2016/0059044 A1 | 3/2016 | Gertner |

OTHER PUBLICATIONS

U.S. Appl. No. 15/661,909, filed Jul. 27, 2017.
International Search Report dated Sep. 9, 2016 in International Application No. PCT/US2016/040776.

* cited by examiner

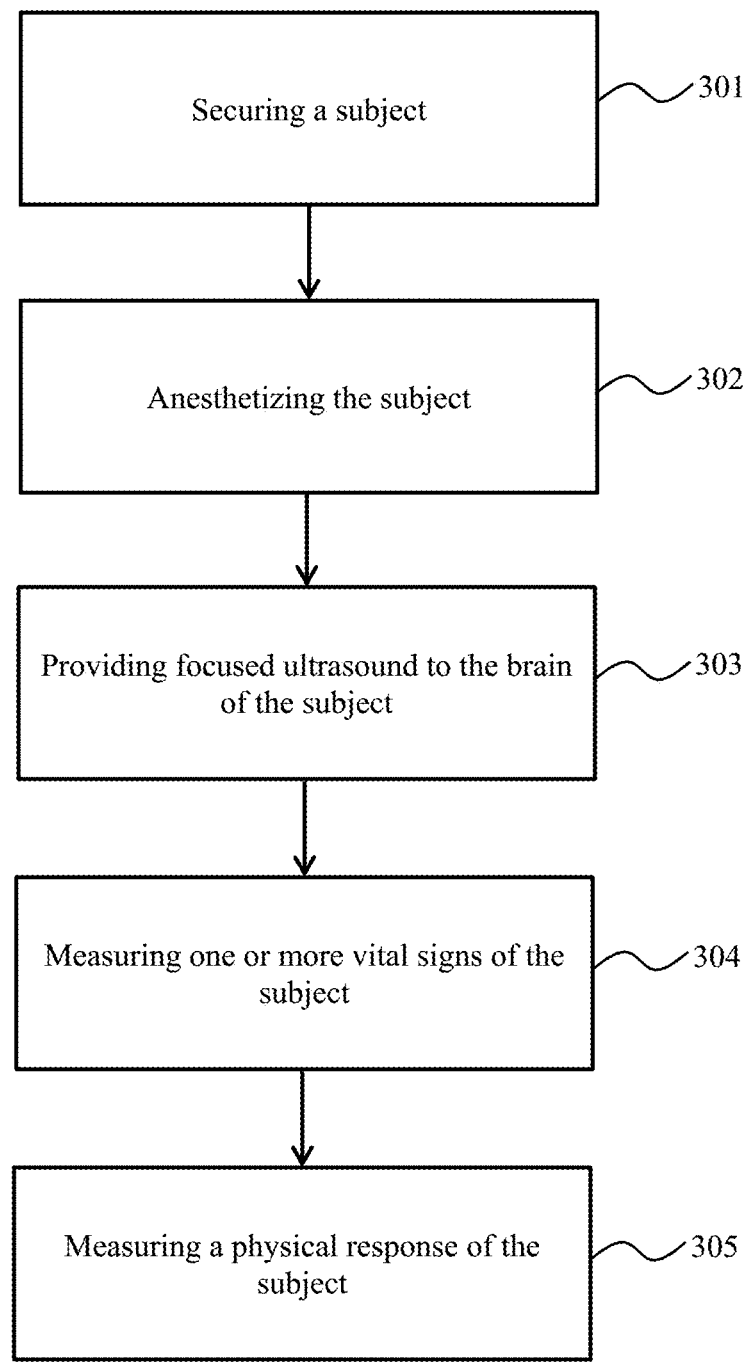

SYSTEMS AND METHODS FOR NON-INVASIVE BRAIN STIMULATION WITH ULTRASOUND

CROSS-REFERENCE TO RELATED APPLICATIONS

This application claims priority to U.S. Provisional Application No. 62/114,321 filed Feb. 10, 2015, which is incorporated by reference herein in its entirety.

STATEMENT REGARDING FEDERALLY-SPONSORED RESEARCH

This invention was made with government support from the National Institutes of Health under Grant Nos. R01-EB009041 and R01-AG038961. The government has certain rights in the invention.

BACKGROUND

Brain stimulation can involve evoking a neural response by touching or otherwise activating the brain, either directly or indirectly. For example, brain stimulation can be used to evoke neuromodulation, which can be used in treating various neurological disorders, as well as other conditions involving the brain, such as psychiatric disorders. Brain stimulation can thus be used to treat neuropathic pain, Parkinson's disease, depression, obsessive-compulsive disorder, essential tremor, and brain tumors, among other disorders. Additionally, systems and techniques for brain stimulation can be used to analyze various conditions, including epilepsy, Alzheimer's disease, multiple sclerosis, hydrocephalus, stroke, trigeminal neuralgia, and traumatic brain injury. Furthermore, neuromodulation can be used in brain mapping techniques.

Deep brain stimulation (DBS) is a brain stimulation technique using electrodes implanted in the brain to transmit electrical impulses to specific parts of the brain. However, DBS can have adverse neuropsychiatric side-effects due at least in part to its invasive nature. Another brain stimulation technique is optogenetics, which involves using light to stimulate genetically modified neurons. However, such gene modification can be challenging and undesirable.

Non-invasive brain stimulation techniques can include transcranial magnetic stimulation (TMS), which can be used to stimulate small regions of the brain using a magnetic field. However, TMS can have poor spatial resolution, and can have inadequate depth penetration. Furthermore, the effects of TMS can be relatively short lasting (e.g., in the millisecond range).

Thus, there remains an opportunity for improved techniques for non-invasive brain stimulation.

SUMMARY

The presently disclosed subject matter provides techniques for non-invasive brain stimulation using focused ultrasound. An exemplary method of non-invasive brain stimulation in the brain of a subject can include securing the subject in a fixed position relative to an ultrasound source and providing a focused ultrasound having one or more ultrasound parameters to a location in the brain of the subject, the location and the one or more ultrasound parameters selected to evoke a physical response of the subject, and measuring the physical response of the subject.

For example, and as embodied herein, the physical response can be one or more of a body movement, an eye movement, and pupil dilation. The location can be within the primary motor cortex, primary somatosensory cortex, superior colliculus, locus coeruleus, hippocampus, abducens nucleus, and/or medial longitudinal fasciculus.

The one or more ultrasound parameters can include a frequency, a target area, and/or an acoustic pressure. The frequency can be from about 0.1 MHz to about 5 MHz. For example, and as embodied herein, the frequency can be about 1.9 MHz. The target area can be from about 0.5 mm to about 5 mm in the lateral direction and from about 2 mm to about 20 mm in the axial direction. The acoustic pressure can be at least equal to a threshold acoustic pressure for evoking the physical response. The method can include determining the threshold acoustic pressure by providing a focused ultrasound having an ultrasound parameter to a location in the brain of the subject corresponding to a physical response, and verifying whether the physical response occurs. The focused ultrasound can be provided as a burst. The burst can have a pulse repetition frequency of greater than about 30 kHz. The burst can have a duty cycle from about 10% to about 60%. Alternatively, the focused ultrasound can be provided as a chirp.

The method can include anesthetizing the subject using sodium barbital. The dosage of sodium barbital can range from about 25 mg/kg to about 100 mg/kg. The subject can remain under anesthesia for more than about 90 minutes.

The method can further include moving transducers relative to the fixed position of the subject in order to target a location in the brain prior to providing the focused ultrasound. Alternatively or additionally, the method can include moving the transducers within a random grid while providing the focused ultrasound to the brain of the subject in order to generate a random raster sonication.

The method can further include measuring one or more vital signs of the subject before, during, and/or after providing the focused ultrasound. The vital signs can include heart rate, respiratory rate, temperature, blood pressure, body motion, and combinations thereof. Measuring the physical response can include recording the physical response.

The method can include receiving an acoustic cavitation emission and determining a type of acoustic cavitation activity based on the acoustic cavitation emission. The acoustic cavitation activity can be stable cavitation and/or inertial cavitation. The method can further include modulating the ultrasound parameter after determining the type of acoustic cavitation activity.

The presently disclosed subject matter also provides systems for non-invasive brain stimulation in the brain of a subject. An exemplary system can include an ultrasound source for providing a focused ultrasound having one or more ultrasound parameters to a location in the brain of the subject, where the location and the ultrasound parameters are selected to evoke a physical response of the subject, at least one camera for measuring the physical response of the subject, and a processor for controlling the ultrasound source and/or the camera.

The ultrasound source can include a function generator, an amplifier, and/or one or more transducers. The system can further include a frame for securing the subject in a fixed position relative to the ultrasound source. The system can further include a 3D positioning system for moving the transducers relative to the fixed position in order to target the location in the brain of the subject.

The camera can be a monochrome camera for recording an eye movement and/or pupil dilation. Alternatively or additionally, the camera can be a digital camera for recording a body movement. The system can further include a vital signs monitor, which can measure the heart rate, respiratory rate, temperature, body motion, and/or blood pressure of the subject.

BRIEF DESCRIPTION OF THE FIGURES

FIG. 3 is a diagram illustrating an exemplary method for non-invasive brain stimulation using focused ultrasound according to the disclosed subject matter.

DETAILED DESCRIPTION

The presently disclosed subject matter provides techniques for non-invasive brain stimulation using focused ultrasound. According to one aspect of the disclosed subject matter, methods and systems for applying focused ultrasound to the brain of a subject to stimulate a response are provided.

Figure 1:
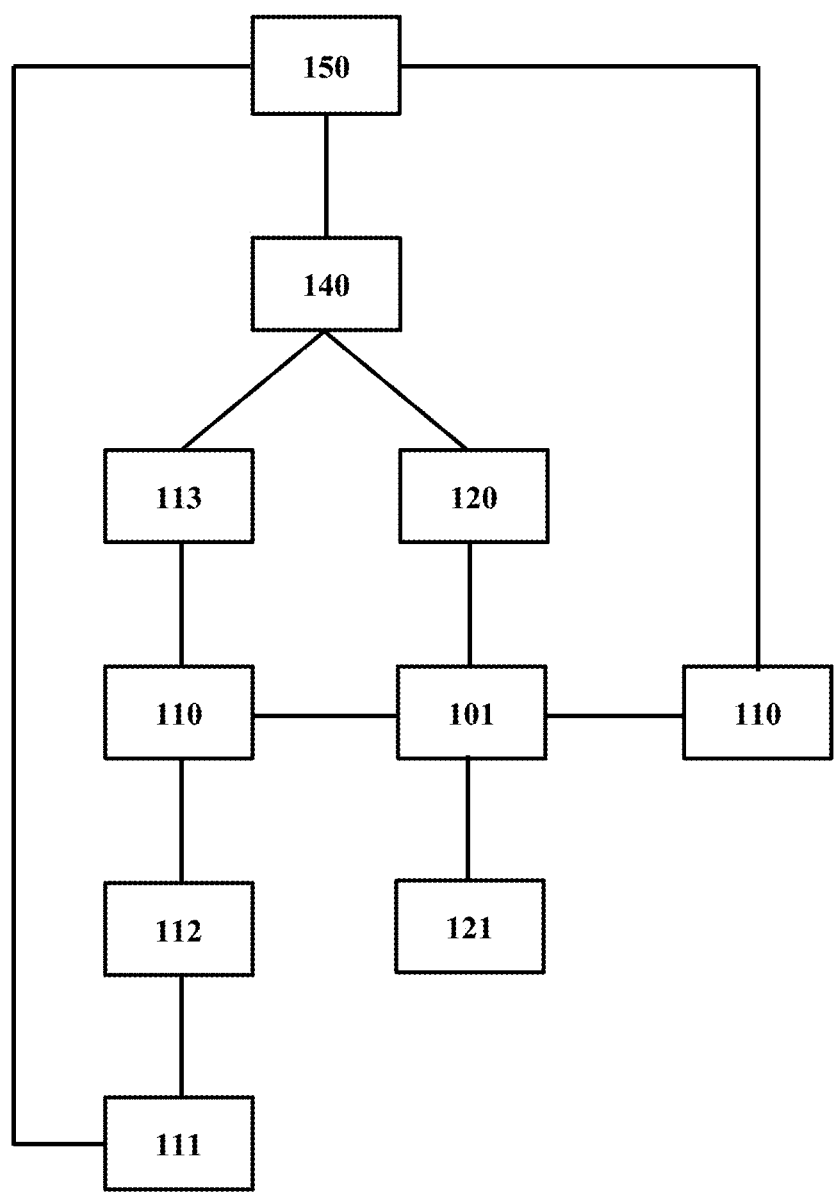
FIG. 1 is a diagram illustrating an exemplary embodiment of a system for non-invasive brain stimulation using focused ultrasound according to the disclosed subject matter.
Figure 2:
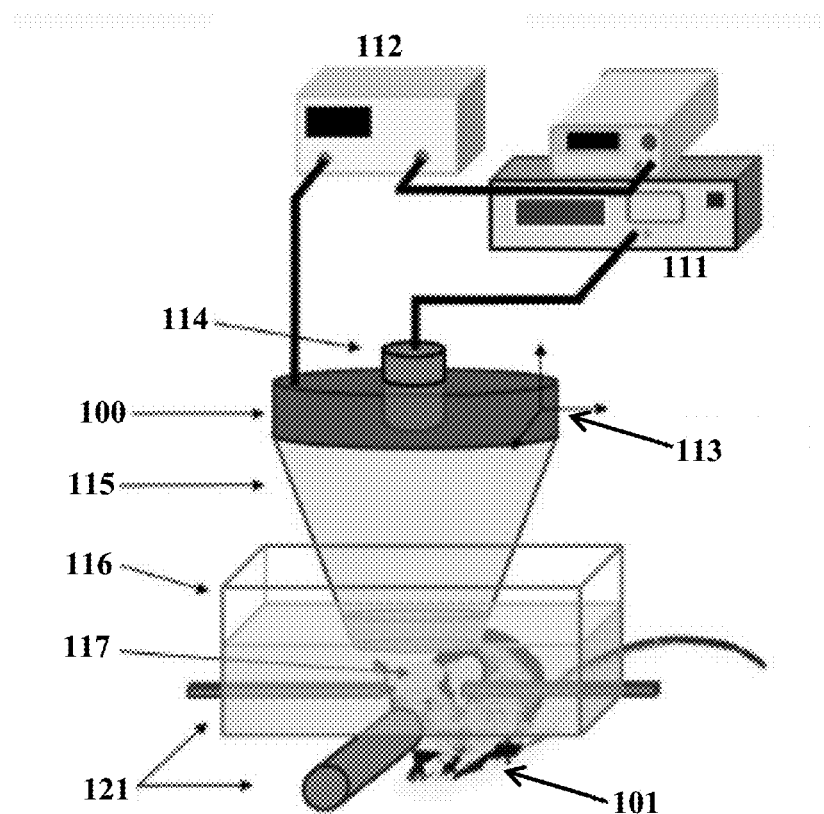
FIG. 2 is a diagram illustrating another embodiment of a system for non-invasive brain stimulation using focused ultrasound according to the disclosed subject matter.

FIG. 1 is a diagram illustrating an exemplary system for non-invasive brain stimulation according to the disclosed subject matter. FIG. 2 is an illustration of an exemplary embodiment of the system of FIG. 1. For purposes of illustration and not limitation, the system of FIG. 1 includes certain additional features that are not illustrated in the embodiment of FIG. 2. Systems according to the disclosed subject matter can include various combinations of some or all of the components of FIG. 1 or 2 according to the desired application(s) and are not limited to the particular combinations of components described herein. With reference to FIGS. 1 and 2, system 100 can include a transducer 110 for providing focused ultrasound to a subject 101.

The disclosed methods and systems can be applied to a variety of living subjects, including humans and animals. For example, and as embodied herein, the subject can be anesthetized. Additionally or alternatively, and as embodied herein, the subject can be secured, for example, to stabilize the target area of the focused ultrasound. System 100 can include various components for securing the subject. For example and without limitation, the system can include one or more restraints 121, such as frames, straps, holders, bars, and/or other features for securing the subject.

According to another embodiment of the disclosed subject matter, a wearable device for providing focused ultrasound to the brain of the subject is provided. The wearable device can include any or all of the features of a system for providing focused ultrasound to the brain as described herein. For example, and as embodied herein, such wearable device can include one or more transducers for providing focused ultrasound, and one or more processors for controlling and targeting the focused ultrasound. A wearable device can further include a vital signs monitor for observing the bodily functions of the subject. Additionally, and as embodied herein, the wearable device can include one or more securing features to secure the wearable device in alignment to provide focused ultrasound to a desired region of the brain. For example and without limitation, the one or more securing features can include straps, buckles, elastic bands, tape, velcro, or any other suitable securing features. In this manner, the securing features can be configured to maintain the desired alignment of the focused ultrasound transducer with respect to the cranial geometry while the subject moves around, and/or can be configured to be applied and removed by the subject without assistance from a clinician.

The disclosed techniques can be used in a wide variety of clinical applications. For example, focused ultrasound can be used to treat varied conditions, including chronic pain, Parkinson's disease, depression, obsessive-compulsive disorder (OCD), obesity, epilepsy, schizophrenia, and essential tremor. In this manner, the configuration of the system and delivery of focused ultrasound can be modified based on the particular condition to be treated. Moreover, either the stationary device or the wearable device described herein, or both such devices, can be used to treat these conditions using the techniques described herein.

For purpose of illustration and not limitation, it can be more convenient for the subject to have a wearable device that can be used without assistance from a clinician. For example, and as embodied herein, certain conditions can be treated using frequent or regular treatments, and thus it can be desirable to allow the treatment to be performed outside a clinical setting, such as and without limitation, in the subject's home. Such conditions can include Parkinson's disease, essential tremor, chronic pain, and brain tumors. For example, a subject diagnosed with a condition can be provided with a wearable device that can be used to perform treatments outside a clinical setting. Focused ultrasound can be provided by the wearable device when symptoms occur and/or pursuant to a predetermined schedule. The wearable device can be pre-programmed with particular ultrasound parameters to treat the subject's condition. Additionally or alternatively, the wearable device can include an interface to permit the ultrasound parameters to be adjusted, for example and without limitation, by the subject or by a clinician. For purpose of illustration and not limitation, for certain conditions, for example and without limitation, essential tremor, the focused ultrasound parameters can be adjusted according to the symptoms experienced by the subject. For example, and as embodied herein, the ultrasound parameters of the wearable device that can be pre-programmed and/or adjusted can include, without limitation, an ultrasound frequency, a duty cycle and/or pulse repetition frequency. In this manner, the wearable device can be configured to provide ultrasound to the subject at the desired ultrasound parameters, for example and without limitation, by modulating a function generator and/or amplifier.

For the treatment of certain conditions, it can be desirable for the subject to receive focused ultrasound within a clinic. For example, certain conditions can be treated with a single treatment or infrequent, periodic treatments that can be performed by a clinician. For purpose of illustration and not limitation, as embodied herein, a stationary device can be used to provide the focused ultrasound to treat various conditions, such as and without limitation, certain psychiatric disorders, including depression, obsessive-compulsive disorder (OCD), and schizophrenia. The stationary device can be used as an alternative to, or in combination with, a wearable device, for example and without limitation, in the treatment of brain tumors.

Referring again to FIGS. 1 and 2, for purpose of illustration and not limitation, system 100 can include a transducer 110 for providing focused ultrasound to a subject 101. The transducer 110 can be a single-element focused ultrasound transducer for providing focused ultrasound. As embodied herein, the transducer 110 can have a focal length of 60 mm and a radius of 30 mm. The transducer can be driven by any suitable equipment, such as a function generator 111. For example, and as embodied herein, function generator 111 can be a 33220A Function/Arbitrary Waveform Generator (Agilent Technologies, Palo Alto, Calif., USA). As embodied herein, function generator 111 can be joined to an amplifier 112, which can increase the power from the generator, e.g., by about 20 dB to about 100 dB, or, as embodied herein, by about 50 dB. In this manner, a signal from the function generator 111 can be amplified by the amplifier, and the transducer can convert the amplified signal into focused ultrasound.

Ultrasound can refer to a sound wave having a frequency above that of human hearing, e.g., greater than 16 kHz. As such, the focused ultrasound for use in the presently disclosed subject matter can have a frequency greater than about 16 kHz, and as embodied herein, can be within a range from about 50 kHz to about 20 MHz. For purpose of illustration and not limitation, the focused ultrasound can have a frequency from about 0.1 MHz to about 5 MHz, or from about 0.5 MHz to about 3 MHz, or from about 1 MHz to about 2 MHz, and as embodied herein, the focused ultrasound can have a frequency of about 1.9 MHz.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The focused ultrasound can be delivered in multiple different forms. For example, and not limitation, the focused ultrasound can be a continuous ultrasound wave. Alternatively, the focused ultrasound can be a chirp, i.e., a swept frequency cosine signal. The swept frequency cosine signal can be linear, quadratic, or logarithmic. Providing the focused ultrasound as a chirp can improve the focus of the ultrasound on a particular location in the brain. Additionally, providing the focused ultrasound as a chirp can inhibit or prevent the formation of standing waves within the brain, which can improve the safety of the focused ultrasound.

As a further example, the focused ultrasound can include one or more pulses, i.e., isolated ultrasound waves. As embodied herein, the focused ultrasound can be a burst, i.e., a sequence of pulses. For example, a burst can have high pulse repetition frequency, e.g., greater than about 30 kHz, greater than about 40 kHz, or greater than about 50 kHz. The burst can have a duty cycle from about 10% to about 60%, or from about 15% to about 40%, and, as embodied herein, the burst can have a duty cycle of about 20%. As embodied herein, the burst can be repeated for at least about 5 cycles, at least about 6 cycles, or at least about 7 cycles.

As embodied herein, and with reference to FIG. 2, system 100 can include one or more chambers 115, 116 containing a couplant, such as oil or water, for transmitting the ultrasound. Additionally or alternatively, a conductive material 117 can be placed on the subject 101. For example, such conductive material includes ultrasound gel and/or water, which is preferably degassed.

The focused ultrasound can impart a certain acoustic pressure onto the brain of the subject. An increased acoustic pressure can increase the ability of the focused ultrasound to elicit a physical response in a subject. However, the acoustic pressure can influence the type and magnitude of acoustic cavitation activity, which can cause neurovascular and neuronal damage in the subject. For these reasons, the acoustic pressure should be calibrated to achieve the desired response without compromising safety. As embodied herein, the acoustic pressure can range from about 0.5 MPa to about 2.5 MPa, from about 0.7 MPa to about 2.25 MPa, or from about 0.75 MPa to about 1.6 MPa. The resulting acoustic cavitation activity can be monitored by receiving cavitation emissions. With reference to FIG. 2, system 100 can include a pulse echo transducer 114 and/or a hydrophone, which can be configured to receive cavitation emissions in active or passive mode.

With continued reference to FIGS. 1 and 2, the transducer 110 can be secured within a 3D positioning system 113, which can be used to align the focused ultrasound from the transducer with a target area on the subject 101. The 3D positioning system can move the transducer in the x-, y-, and z-directions. For example, the 3D positioning system can include a motor and a controller. For purpose of illustration and not limitation, and as embodied herein, the controller can include a VXM™ Controller (Velmex Inc., New York, N.Y., USA).

As embodied herein, the 3D positioning system 113 can move the transducer 110, for example and without limitation, within a predefined grid. The size and resolution of the predefined grid can be selected by the user. For example, and as embodied herein, the grid can be 8 mm by 8 mm and can have a resolution of 1 mm. The grid can be centered of a specific region of the brain, for example, as defined relative to the bregma and/or the lambda. A person having ordinary skill in the art will appreciate that the center of the grid can correspond to the region of the brain targeted for the focused ultrasound, and thus the center of the grid will depend on the study or neurostimulation being performed. The 3D positioning system 113 can move the transducer 110 within the grid to produce a random raster sonication on the subject 101 using the focused ultrasound.

Referring still to FIG. 1, system 100 can include a vital signs monitor 120 for monitoring one or more vital signs of the subject 101. By way of example, and not limitation, the vital signs monitor can measure the state of one or more bodily functions, e.g., heart rate, respiratory rate, body temperature, body motion, and/or blood pressure. Additionally or alternatively, the vital signs monitor can include one or more components for measuring bodily functions, e.g., thermometers, gauges, sensors, transmitters, and receivers. The components of the vital signs monitor and/or the bodily functions measured can be configured for different applications, for example based on the size, age, and species of the subject.

With continued reference to FIG. 1, system 100 can include one or more cameras 130. Camera(s) 130 can be used to record any physical responses in the subject 101 during brain stimulation. Additionally or alternatively, the one or more cameras can also be used to record the resting state of the subject. The one or more cameras can be capable of capturing video and/or still images. The cameras can be capable of capturing digital images. For example, and as embodied herein, system 100 can include at least one monochrome camera. A monochrome camera can be used, for example, to record pupil dilation and eye movement in the subject. For example and as embodied herein, camera 130 can include Model DMK 23U618 (The Imaging Source GmbH, Bremen, Germany), or any suitable camera. Additionally or alternatively, the system can include at least one digital camera. The digital camera can be used, for example, to record body movements in the subject, e.g., movements of limbs, paws, hands, tails or other extremities. Exemplary digital cameras can include Model EOS Rebel T3i (Canon, Melville, N.Y., USA), and/or web cameras, such as Model C920 (Logitech, Calif., USA), or any other suitable digital camera.

Referring still to FIG. 1, system 100 can include a processor 140. The processor can be configured to carry out the instructions specified by software stored in a hard drive, a removable storage medium, or any other storage media. The software can include computer codes, which can be written in a variety of languages, e.g., Matlab and/or Microsoft Visual C++. Additionally or alternately, the processor can include hardware logic, such as logic implemented in an application-specific integrated circuit (ASIC). The processor 140 can be configured to control one or more of the system components described above. For example, and as embodied herein, the processor 140 can be configured to control the output of the function generator 111 and/or the transducer 110 to provide the focused ultrasound to the subject 101. Additionally or alternatively, the processor 140 can instruct a controller within the 3D positioning system 113. The processor 140 can also be configured to control the one or more cameras 130.

With continued reference to FIG. 1, the processor 140 can be configured to receive information from one or more system components. For example, the processor 140 can receive one or more images from the one or more cameras 130. The processor 140 can also receive one or more measurements from the vital signs monitor 120. Additionally or alternatively, the processor 140 can be configured to transmit such information to an acquisition board 150 for storage. Non-limiting examples of suitable acquisition boards include Gage (DynamicSignals LLC, Lockport, Ill., USA) and MP150 (Biopac Systems Inc., Santa Barbara, Calif., USA).

System 100 can be used to target a desired area of the brain for stimulation, which can be any area of the brain. For purpose of illustration and not limitation, as embodied herein, system 100 can be used to target cortical and subcortical regions of the brain, e.g., the primary motor cortex, primary somatosensory cortex, superior colliculus, locus coeruleus, hippocampus, abducens nucleus, medial longitudinal fasciculus.

As embodied herein, system 100 can have high target specificity, and can achieve a resolution in the millimeter range. For example, and as embodied herein, system 100 can provide focused ultrasound to a target area that is from about 0.5 mm to about 5 mm, or from about 0.75 mm to about 2 mm, or about 1 mm in the lateral direction (i.e., in diameter) and from about 2 mm to about 20 mm, or from about 5 mm to about 15 mm, or about 10 mm in the axial direction. This high target specificity can enable the focused ultrasound to target a specific region of the brain corresponding to a particular physical response.

According to another aspect of the disclosed subject matter, methods for non-invasive brain stimulation are provided. FIG. 3 illustrates an exemplary method according to the disclosed subject matter. The method 300 can include securing a subject 301 and providing focused ultrasound to the brain of the subject 303.

The subject can be secured such that the target area of the focused ultrasound, i.e., the brain, remains still. For example, and as embodied herein, the subject can be secured using the restraints described above. Additionally or alternatively, the method 300 can include anesthetizing the subject 302. When the method includes both securing and anesthetizing the subject, the steps can be performed in either order. For example, the subject can be secured prior to being anesthetized, or alternatively, the subject can be secured after being anesthetized.

For purpose of illustration and not limitation, the performance of brain stimulation using focused ultrasound can be affected at least in part by the type of anesthesia used. For example, selecting an anesthetic that reduces or limits suppression of evoked responses can be desirable when targeting certain areas of the brain. For example, sodium pentobarbital can be a suitable anesthetic to target the cortex. For purpose of illustration and comparison, and not limitation, sodium pentobarbital can suppress cortical evoked responses less than certain other anesthetics, e.g., isoflurane. Additionally, for purpose of illustration and comparison, and not limitation, sodium pentobarbital can last longer than certain other anesthetics, e.g., ketamine. Furthermore, using light amounts of certain anesthetics such as isoflurane or ketamine can result in spontaneous movements, which can be confused with the evoked responses, and thus can affect the performance of brain stimulation described herein.

For example, and as embodied herein, the subject can be anesthetized using sodium pentobarbital. The sodium pentobarbital can be provided in a certain dosage relative to the body weight of the subject. For example, and as embodied herein, the dosage can be from about 25 mg/kg to about 100 mg/kg, or from about 50 mg/kg to about 75 mg/kg, or about 65 mg/kg. The method can include waiting a certain resting period for the anesthesia to take effect. By way of example, the resting period can be from about 20 minutes to about 30 minutes. The sodium pentobarbital can remain in effect for a certain period, e.g., up to 60 minutes, up to 90 minutes, up to 2 hours, or up to 2.5 hours.

With continued reference to FIG. 3, the method 300 can further include providing focused ultrasound to the brain of the subject 303. The focused ultrasound have various ultrasound parameters. For example, and as embodied herein, ultrasound parameter can include at least one of the frequency, the target area, the acoustic pressure, and/or the duty cycle of the focused ultrasound. The focused ultrasound can have a frequency from about 1 MHz to about 5 MHz, or from about 1 MHz to about 3 MHz, or from about 1 MHz to about 2 MHz, or as embodied herein, of about 1.9 MHz. Additionally, and as embodied herein, the focused ultrasound can have a target area that is from about 0.5 mm to about 5 mm in the lateral direction and from about 2 mm to about 20 mm in the axial direction.

The focused ultrasound can be targeted at a location within the brain of the subject. Particular regions of the brain can correspond to certain physical responses, and thus the focused ultrasound can be targeted at a particular location to evoke a particular physical response. For example, the focused ultrasound can be targeted at locations within the cortical and subcortical regions of the brain, e.g., the primary motor cortex, primary somatosensory cortex, superior colliculus, locus coeruleus, hippocampus, abducens nucleus, medial longitudinal fasciculus. Additionally, the focused ultrasound can be provided at a certain acoustic pressure in order to evoke the response, which can depend at least in part, e.g., on the type of physical response and the location within the brain. The acoustic pressure to evoke a physical response can be referred to as the "threshold acoustic pressure." The threshold acoustic pressure can be determined using the techniques described herein.

As embodied herein, the method can include providing a focused ultrasound having a certain acoustic pressure to a location within the brain of the subject to evoke a physical response corresponding to that location. The acoustic pressure can be greater than or equal to the threshold acoustic pressure to evoke the physical response at that location.

With further reference to FIG. 3, the method 300 can include measuring one or more vital signs of the subject 304. For example, the heart rate, respiratory rate, body temperature, body motion, and/or blood pressure of the subject can be measured, e.g., using a vital signs monitor as described above. Measuring the vital signs of the subject can occur before, during, and/or after providing focused ultrasound to the brain of the subject 303.

For example, and as embodied herein, the measured vital sign(s) of the subject can be used to detect whether the subject has been fully anesthetized. As such, the focused ultrasound can be provided after the subject has been fully anesthetized. By way of example, and not limitation, the subject can be considered fully anesthetized when its heart rate and/or respiratory rate are below a threshold, and as embodied herein, the threshold can depend on the characteristics of the subject, e.g., the age, species, or any other suitable characteristics of the subject. For example, and as embodied herein, a mouse subject can be considered fully anesthetized when its heart rate is below 200 beats per minute (bpm) and/or its respiratory rate is below 70 breaths per minute (brpm).

Additionally or alternatively, the measured vital sign(s) of the subject can be used to monitor the bodily function of the subject while providing focused ultrasound. In this manner, the method can detect any changes in the bodily function of the subject during brain stimulation. The measured vital sign(s) can be used to detect any irregularities in the subject that may have been caused by the brain stimulation.

In addition, or as a further alternative, the measured vital sign(s) of the subject can be used to determine the status of the subject after providing the focused ultrasound. For example, measuring the vital signs can be used to determine whether the brain stimulation has resulted in any long-term changes in bodily function.

With further reference to FIG. 3, the method 300 can include measuring a physical response of the subject 305. For example, and as embodied herein, a physical response can include a body and/or eye movement and/or pupil dilation. By way of example, and not limitation, a body movement can include front or hind limb, paw, hand, or leg movement and/or tail movement or rotation. The physical response can be measured directly and/or with the aid of a camera.

For example, and as embodied herein, measuring the physical response can include recording the physical response using a camera. For example, and not limitation, and as described above, eye movement and/or pupil dilations can be recorded using a monochrome camera and body movements, e.g., limb movement, paw movement, or tail movement, can be recorded using a digital camera.

As discussed above, focused ultrasound imparts a certain acoustic pressure onto the brain of the subject, which can influence acoustic cavitation activity. Thus, in certain aspects, the method can include monitoring acoustic cavitation activity in the brain of the subject. Monitoring acoustic cavitation activity within the brain of the subject can permit acoustic pressure of the focused ultrasound to be properly calibrated to avoid adverse effects. Exemplary techniques and systems for monitoring acoustic cavitation activity are disclosed at International Patent Application Publication Nos. WO2011035312A1 and WO2010030819A1 and U.S. Patent Application Publication Nos. 2015/0065871, 2015/0045724 and 2014/0114216, each of which incorporated by reference herein in its entirety.

As embodied herein, monitoring acoustic cavitation activity can include detecting cavitation emissions to determine the presence and/or location of acoustic cavitation. By way of example, and not limitation, a transducer can passively receive such cavitation emissions. Certain cavitation emissions can indicate the presence of cavitation. For example, broadband emissions can indicate the presence of inertial cavitation, whereas harmonic, subharmonic, or ultraharmonic emissions can indicate the presence of stable cavitation. Methods can further include modulating an ultrasound parameter, e.g., the frequency, target area, acoustic pressure, and/or duty cycle, of the focused ultrasound after determining the type or presence of acoustic cavitation activity.

The systems and techniques of the disclosed subject matter provide advantages over certain existing technologies. For purpose of illustration and not limitation, advantages of the systems and techniques described herein include high target specificity, non-invasive procedures, and improved methods of anesthetizing a subject. Additionally, the systems and techniques described herein provide non-invasive techniques for brain stimulation having applications in neuroscience, including brain mapping, medical treatment, and therapy. For example and without limitation, the systems and techniques disclosed herein can be used in the treatment of chronic pain, Parkinson's disease, depression, obesity, epilepsy, obsessive-compulsive disorder (OCD), schizophrenia, and essential tremor. Additionally, the systems and techniques disclosed herein can be used during high-intensity focused ultrasound (HIFU) treatment to provide increased target specificity while avoiding sensory effects, e.g., paresthesia of the lips and/or fingers.

EXAMPLES

For purpose of illustration and confirmation of the disclosed subject matter, and without limitation, exemplary techniques for non-invasive brain stimulation are further illustrated with reference to the examples below. Although the exemplary techniques are described with respect to a mouse subject, the techniques described herein can be applied to perform brain stimulation in any subject, including mammals, such as humans.

Example 1

This exemplary technique was performed on C57BL-6 mice. The mice were anesthetized with an intraperitoneal injection of sodium pentobarbital (65 mg/kg). The animals remained in the cage for a period of 20 to 30 minutes to allow the anesthesia to take effect. The effect of the anesthesia was assessed by pedal reflex and vital signs recordings. The animals were shaved (on the scalp and on the throat) and positioned in a 3-axes stereotaxic frame (e.g., David Kopf Instruments, Tujunga, Calif., USA) using ear bars and a teeth holder. Oxygen was delivered continuously via a mask.

A vital signs monitor (e.g., MouseOx Plus, Starr Life Sciences Corp., Torrington, Conn., USA) was placed on the throat of the animals to assess their heart rates and respiratory rates before and during sonication. Focused ultrasound was applied when the heart rate and respiratory rate were less than 200 bpm and 70 brpm. During sonication, the heart rate and respiratory rate were respectively less than 400 bpm and 120 brpm.

A single-element focused ultrasound transducer was driven by a function generator (e.g., 33220A, Agilent Technologies, Palo Alto, Calif., USA), through a 50 dB power amplifier (e.g., ENI Inc., Rochester, N.Y., USA). The sonications were carried out at 1.9 MHz with a 50% duty cycle, a pulse repetition frequency of 1 kHz, a sonication duration of 1 second and interstimulus interval of 1 second, and was repeated 10 times for each sonication spot. The transducer was fixed in a 3D positioning system (e.g., VXM, Velmex Inc, New York, N.Y., USA) and moved randomly within a grid of 8 mm by 8 mm with a resolution of 1 mm. The center of the grid was placed at anteroposterior (AP)=−2 mm and mediolateral (ML)=0 mm from lambda.

The vital signs were recorded during the sonication using an acquisition board (e.g., MP150, Biopac Systems Inc., Santa Barbara, Calif., USA), which was triggered by the same function generator used to drive the ultrasound transducer. Some paw movements were observed in the animals. Videos of the evoked paw movements were recorded by cameras positioned on the backs of the animals (e.g., model C920, Logitech, Calif., USA and model EOS Rebel T3i, Canon, Melville, N.Y., USA). Additionally, pupil dilation were observed, and recorded using a second camera (e.g., Model DMK 23U618, The Imaging Source GmbH, Bremen, Germany), which was positioned beside the mice and trained on the right eye. Muscle activity was measured using an electromyography (EMG) system (e.g., BN-EMG2, Biopac Systems Inc., Santa Barbara, Calif., USA) with 26-gauge electrodes placed 5 mm apart at the biceps femoris of both hind limbs and the ground electrode on the tail.

The animals remained under anesthesia for about 90 minutes, and were not responsive to pinches at any time. At approximately 30 minutes after the anesthesia took effect (e.g., between 30 minutes and 60 minutes after injection), no motor response was observed in certain animals. Thereafter, the first signs of evoked motor responses and pupil dilations were observed. The working time lasted about 60 minutes after this first stage of anesthesia.

Figure 4A:
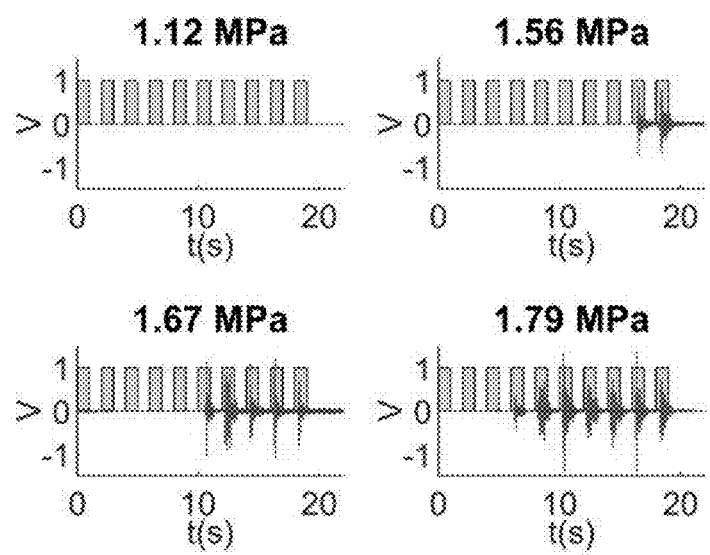
FIG. 4A is a diagram illustrating multiple electromyography (EMG) graphs indicating contralateral responses in mice during brain stimulation at various acoustic pressures.
Figure 4B:
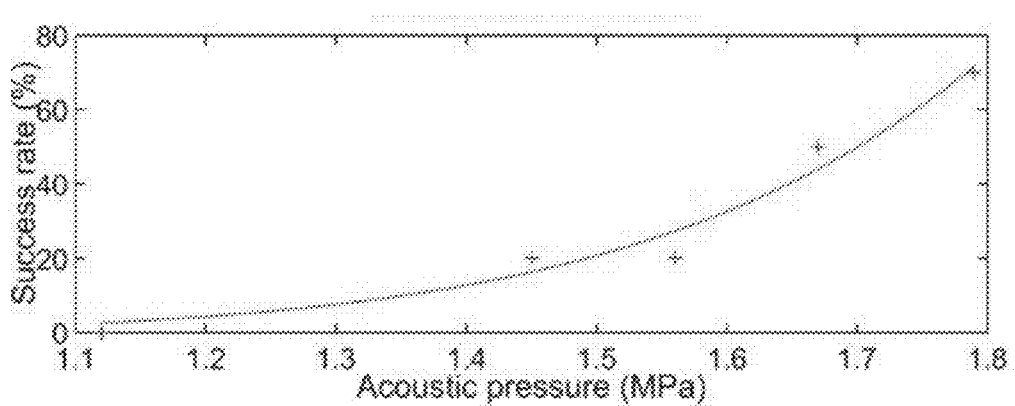
FIG. 4B is a diagram illustrating the success rate of evoking a physical response with focused ultrasound at acoustic pressures ranging from 1.1 MPa to 1.8 MPa.
Figure 4C:
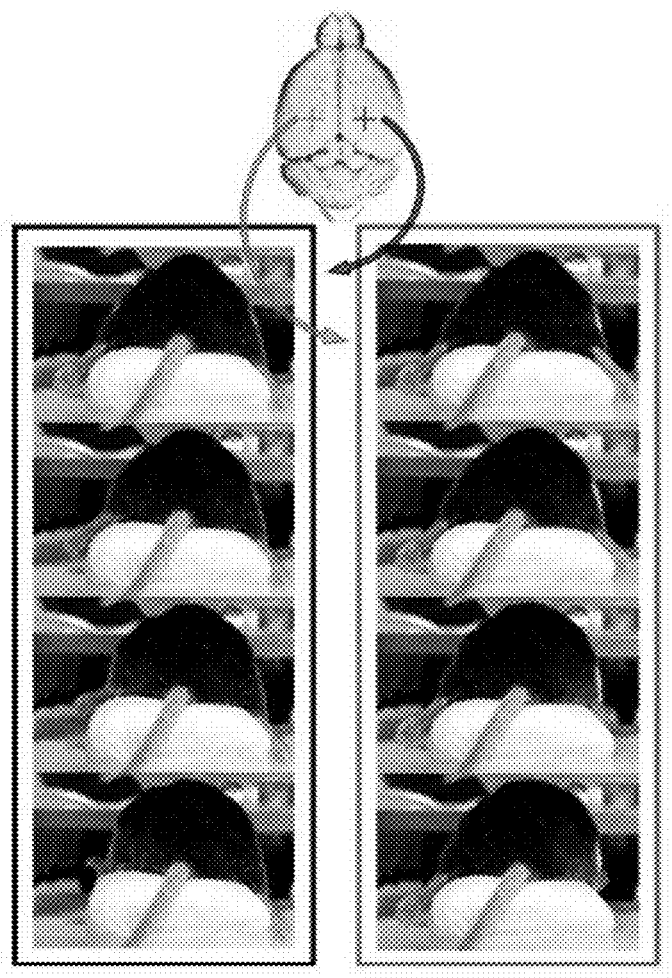
FIG. 4C depicts two series of images illustrating contralateral paw movement in response to focused ultrasound.

Contralateral muscle activity recorded on EMG signals was observed when ultrasound neurostimulation was carried out at +2 mm of lambda and ±2 mm lateral of the midline. The minimum pressure to elicit movements was 1.45 MPa, which was calibrated using an excised skull. Increasing the pressure increased the success rate from 20% (at 1.45 MPa) to 70% (at 1.79 MPa). The estimated latency was 266±37 milliseconds. FIG. 4A is a diagram illustrating the EMG of the right hind limb, showing contralateral responses at different acoustic pressures. FIG. 4B illustrates the trend line of the success rate across several acoustic pressures ranging from 1.1 MPa to 1.8 MPa. FIG. 4C depicts two series of video frames showing contralateral paw movement. The left-most series shows left paw movement when sonicating at anterior/posterior (AP)=+2 mm from lambda and medial/lateral (ML)=+2 mm. The right-most series shows right paw movement when sonicating at AP=+2 mm from lambda and ML=−2 mm.

Figure 5A:
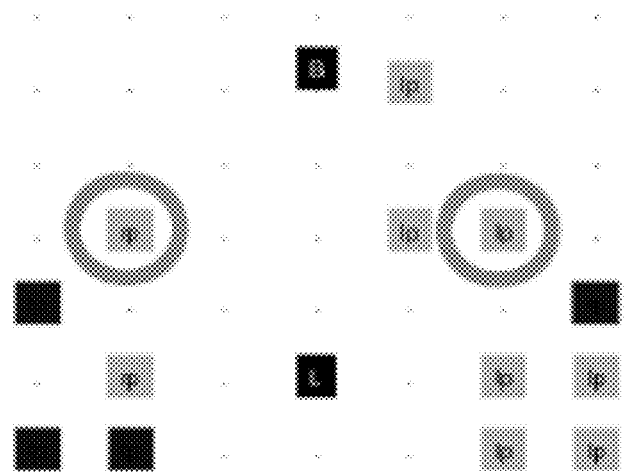
FIGS. 5A-5B are diagrams illustrating the location of two sonications, and indicating where contralateral and ipsilateral paw movements were observed.
Figure 5B:
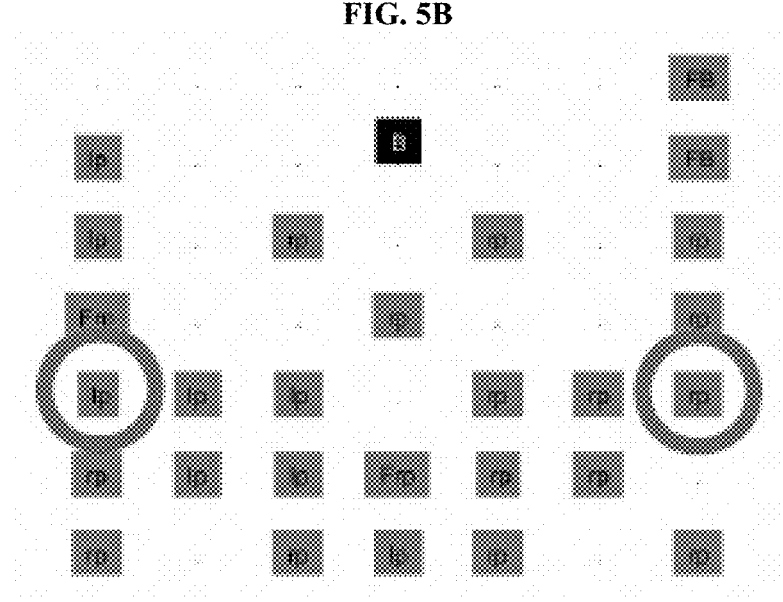

Additional paw movements were observed and recorded on video. The transducer being was successfully used to sonicate first the left side of the brain and, immediately after, the opposite side, both of which elicited contralateral paw movements. Further, ipsilateral hind limb movements were elicited when sonications were carried out at 0 mm from lambda and ±3 mm lateral of the midline. Additionally, tail movements were observed. The diagram of FIG. 5A depicts a grid, showing responses with sonications at AP=+/−2 mm from lambda and ML=+/−2 mm. The diagram of FIG. 5B depicts a grid, showing responses with sonications at AP=+/−1 mm from lambda and ML=+/−3 mm. The black squares in the center represent the lambda and the bregna. Darker squares indicate ipsilateral movement, while lighter squares indicate contralateral movement. The circles indicate the areas of the brain where neuromodulation was recorded.

Figure 6A:
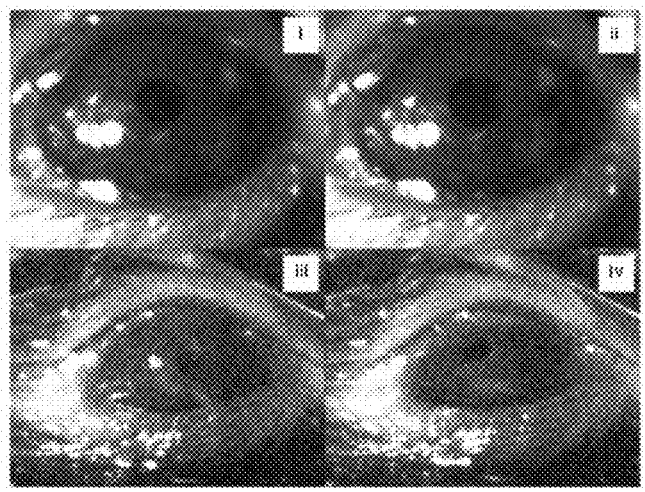
FIG. 6A depicts two series of images illustrating pupil dilation and eye movement in response to focused ultrasound.
Figure 6B:
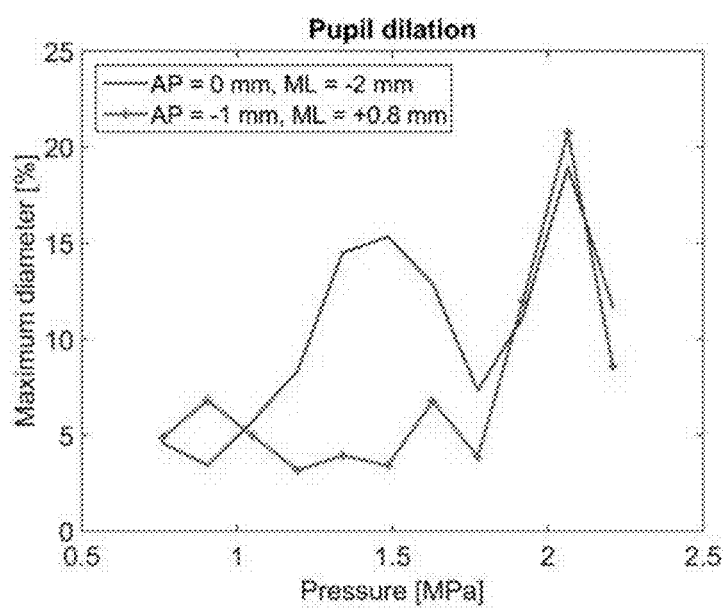
FIG. 6B is a diagram illustrating pupil dilation at various acoustic pressures for focused ultrasound at two different regions in the brain.

Using the second camera, pupil dilations and eye movements were observed and recorded on video. For example, FIG. 6A depicts still images from the video recording. The top two images of FIG. 6A show pupil dilation of up to 20% and the bottom two images show eye movement. These pupil dilation and eye movements were observed when sonications were carried out at AP=0 mm from lambda and ML=+2 mm. Additionally, the acoustic pressure thresholds varied depending on the placement of the sonications. For example, FIG. 6B represents pupil dilation at different acoustic pressures for sonications carried out at AP=0 mm from lambda and ML=±2 mm, as well as sonications carried out at AP=−1 mm from lambda and ML=±0.8 mm. As shown, for example, in FIG. 6B, the sonications performed at AP=0 mm from lambda and ML=±2 mm evoked pupil dilation at a lower acoustic pressure compared to the sonications performed at AP=−1 mm from lambda and ML=±0.8 mm.

Figure 7A:
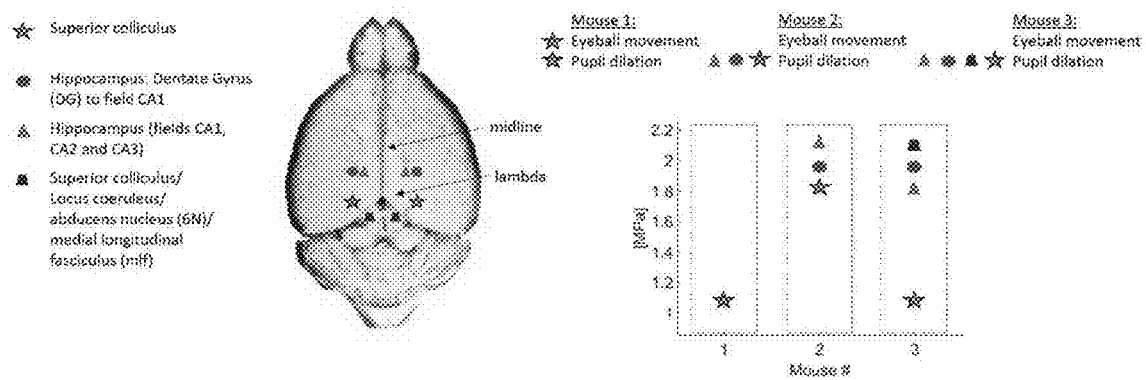
FIG. 7A is a diagram illustrating locations where focused ultrasound evoked pupil dilation and/or eyeball movement, and the corresponding threshold acoustic pressures.
Figure 7B:
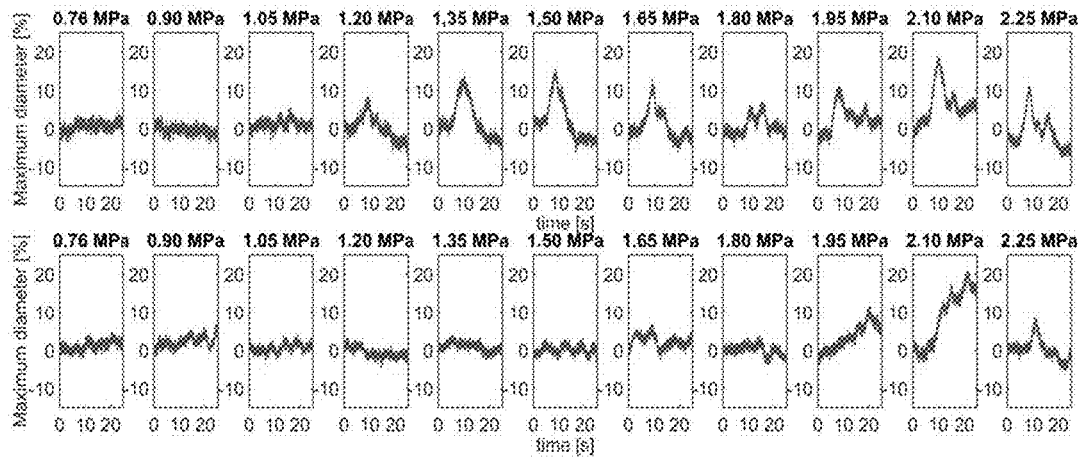
FIG. 7B includes diagrams illustrating the maximum pupil dilation observed at various acoustic pressures for focused ultrasound at two different regions in the brain.

FIG. 7A is a diagram illustrating the sonication locations where pupil dilation and/or eyeball movement were observed, and the corresponding threshold acoustic pressure. Various eye motor-related and anxiety-related regions of the brain (e.g., the superior colliculus, the hippocampus, the superior colliculus, the locus coeruleus, the abducens nucleus, and the medial longitudinal fasciculus) were swept by focused ultrasound having a target area of 8.73 mm long with a 1.02 mm diameter. FIG. 7B is a series of diagrams illustrating the maximum pupil dilation at various acoustic pressures for sonications at AP=0 mm from lambda and ML=±2 mm, i.e., the superior colliculus (top series of images), as well as sonications at AP=−1 mm from lambda and ML=±0.8 mm, e.g., the locus coeruleus (bottom series of images). The superior colliculus elicited pupil dilation at a lower threshold (e.g., 1.20 MPa). Other regions, e.g., those that have been linked to anxiety such as the hippocampus and locus coeruleus, elicited pupil dilations at higher acoustic pressure thresholds (e.g., greater than 1.8 MPa).

Whole brain histological examinations using hematoxylin and eosin (H&E) staining for general histology showed no brain damage in five mice that were sonicated at 1.93 MPa at AP=+2 mm from lambda and ML=+2 mm and again with 3.0 MPa at AP=+2 mm from lambda and ML=−2 mm, indicating that the techniques described herein do not cause neurovascular or neuronal damage.

Example 2

This exemplary technique uses various forms of focused ultrasound while monitoring the acoustic pressure in the brain of the subject. Six C57BL-6 mice were prepared for sonication as described herein in Example 1.

Various forms of focused ultrasound were delivered to the mice. For the first mouse, focused ultrasound was delivered as a continuous wave. A burst of 7 cycles was delivered to the second mouse. The third mouse received a high pulse-repetition frequency burst, i.e., having a pulse-repetition frequency of 50 kHz and a duty cycle of 20% for five cycles. The remaining mice received a focused ultrasound chirp, which was a linearly, quadratically, or logarithmically swept-frequency cosine signal.

Figure 8A:
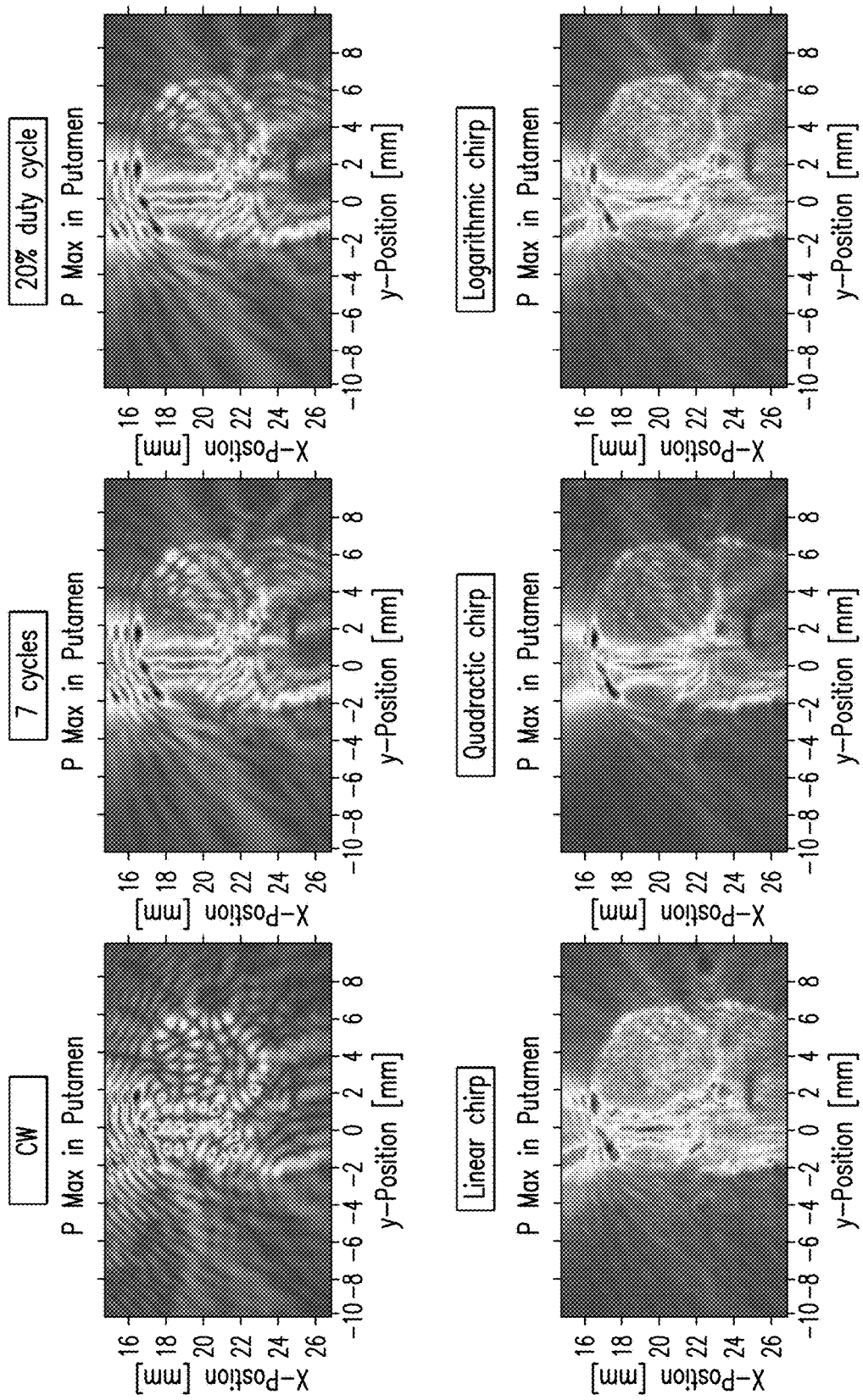
FIG. 8A is a diagram illustrating acoustic pressure fields within mouse brains that were subjected to six different forms of focused ultrasound.
Figure 8B:
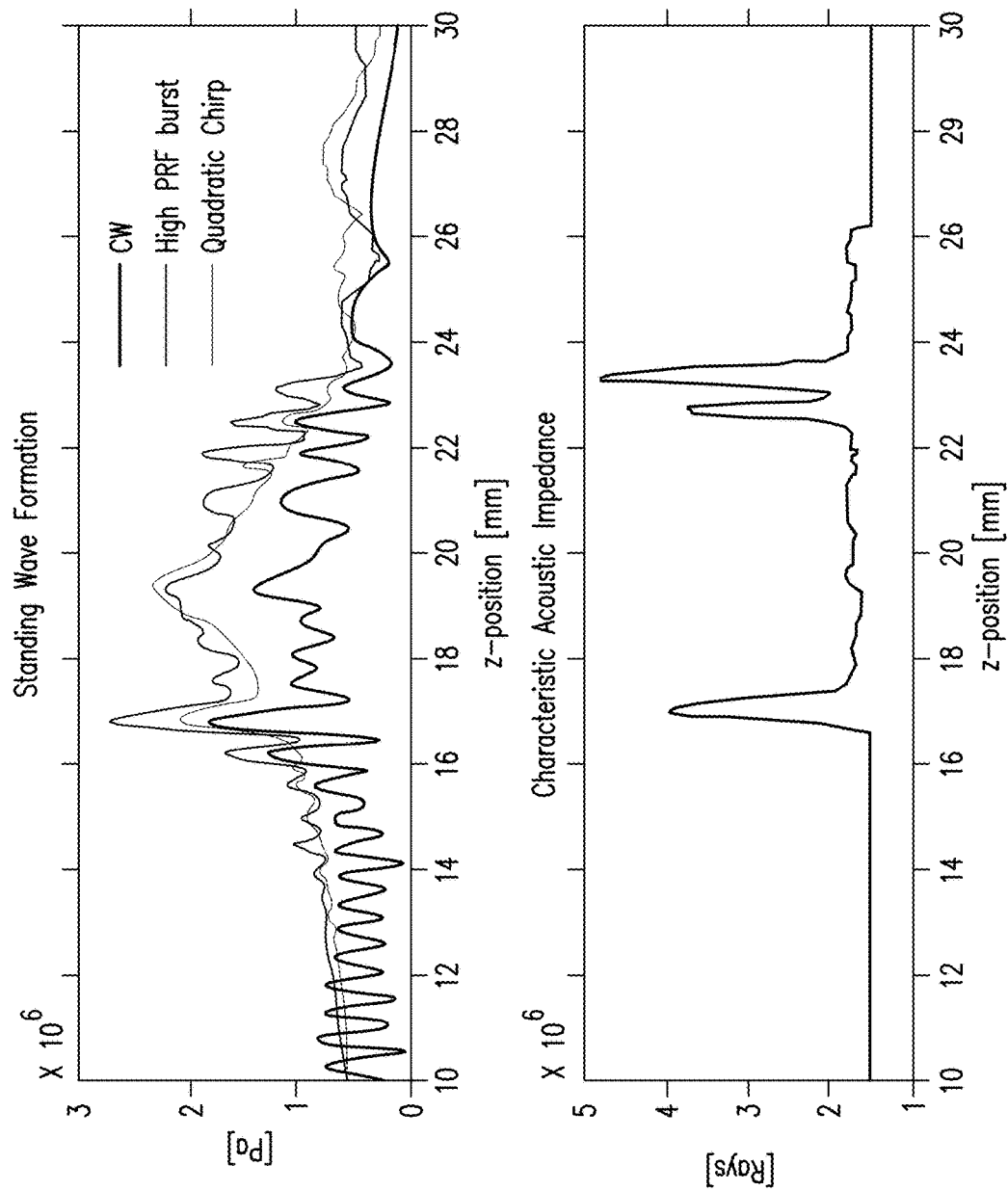
FIG. 8B is a diagram illustrating the acoustic pressure along the axial path of the focused ultrasound, when the focused ultrasound was provided as a continuous wave, a high pulse-repetition frequency burst, and a quadratic chirp.

FIG. 8A depicts the acoustic pressure fields within the brain of each mouse after each form of focused ultrasound. The ultrasound was focused at AP=+6 mm, ML=2.2 mm, and a 3 mm depth. FIG. 8B depicts the acoustic pressure along the axial path of the focused ultrasound for the continuous wave, the high pulse-repetition frequency burst, and the quadratic chirp. The lower plot in FIG. 8B shows the acoustic impedance to indicate the location of the skull. Such techniques can be used to monitor the acoustic pressure with the brain of the subject, and to determine the appropriate form of ultrasound for the desired application.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the methods and systems of the disclosed subject matter without departing from the spirit or scope of the disclosed subject matter. Thus, it is intended that the disclosed subject matter include modifications and variations that are within the scope of the appended claims and their equivalents.

What is claimed is:

1. A method for non-invasive brain stimulation in a brain of a subject, comprising:
    securing an ultrasound source in a fixed position relative to the subject;
    providing a focused ultrasound having one or more ultrasound parameters to a location in the brain of the subject, the location and the one or more ultrasound parameters selected to evoke a physical response of the subject, the one or more ultrasound parameters comprising at least one of a frequency, a target area, and an acoustic pressure, and wherein:
    the frequency is from about 1 MHz to about 5 MHz;
    the target area is from about 0.5 mm to about 5 mm in the lateral direction and from about 2 mm to about 20 mm in the axial direction; and
    the acoustic pressure is at least equal to a threshold acoustic pressure for evoking the physical response; and
    measuring the physical response of the subject wherein the physical response comprises at least one of a body movement, an eye movement, and pupil dilation.

2. The method of claim 1, wherein the location is within at least one of the primary motor cortex, primary somatosensory cortex, superior colliculus, locus coeruleus, hippocampus, abducens nucleus, and medial longitudinal fasciculus.

3. The method of claim 1, wherein the frequency is about 1.9 MHz.

4. The method of claim 1, further comprising determining the threshold acoustic pressure by providing a focused ultrasound having an ultrasound parameter to a location in the brain of the subject, wherein the location corresponds to a physical response, and verifying whether the physical response occurs.

5. The method of claim 1, wherein the focused ultrasound is provided as a burst having a pulse repetition frequency and a duty cycle.

6. The method of claim 5, wherein the pulse repetition frequency is greater than about 30 kHz.

7. The method of claim 5, wherein the duty cycle is from about 10% to about 60%.

8. The method of claim 1, wherein the focused ultrasound is provided as a chirp.

9. The method of claim 1, further comprising anesthetizing the subject using an amount of sodium barbital.

10. The method of claim 9, wherein the amount of sodium barbital ranges from about 25 mg/kg to about 100 mg/kg.

11. The method of claim 9, wherein the subject remains under anesthesia for more than about 90 minutes.

12. The method of claim 1, wherein the measuring further comprises moving one or more transducers relative to the fixed position to target the location in the brain of the subject prior to providing a focused ultrasound.

13. The method of claim 12, wherein the measuring further comprises moving the one or more transducers within a random grid while providing the focused ultrasound to generate a random raster sonication.

14. The method of claim 1, further comprising measuring one or more vital signs of the subject before, during, and/or after providing the focused ultrasound.

15. The method of claim 14, wherein the one or more vital signs are selected from the group consisting of heart rate, respiratory rate, temperature, body motion, blood pressure, and combinations thereof.

16. The method of claim 1, wherein the measuring the physical response comprises recording the physical response.

17. The method of claim 1, further comprising receiving an acoustic cavitation emission and determining a type of acoustic cavitation activity based on the acoustic cavitation emission.

18. The method of claim 17, wherein the acoustic cavitation activity is stable cavitation.

19. The method of claim 17, wherein the acoustic cavitation is inertial cavitation.

20. The method of claim 17, further comprising modulating the ultrasound parameter after determining the type of acoustic cavitation activity.

21. A system for non-invasive brain stimulation in a brain of a subject, comprising:
an ultrasound source for providing a focused ultrasound having one or more ultrasound parameters to a location in the brain of the subject, the location and the one or more ultrasound parameters selected to evoke a physical response of the subject, and the one or more ultrasound parameters comprising a frequency, a target area, and an acoustic pressure, and wherein:
the frequency is from about 1 MHz to about 5 MHz;
the target area is from about 0.5 mm to about 5 mm in the lateral direction and from about 2 mm to about 20 mm in the axial direction; and
the acoustic pressure is at least equal to a threshold acoustic pressure for evoking the physical response, wherein the physical response comprises at least one of a body movement, an eye movement, and pupil dilation: and
a processor for controlling the ultrasound source.

22. The system of claim 21, wherein the ultrasound source comprises a function generator, an amplifier, and one or more transducers.

23. The system of claim 22, further comprising a frame for securing the subject in a fixed position relative to the ultrasound source.

24. The system of claim 23, further comprising a 3D positioning system for moving the one or more transducers relative to the fixed position to target the location in the brain of the subject.

25. The system of claim 21, further comprising a vital signs monitor for measuring at least one of a heart rate, a respiratory rate, a temperature, a body motion, and a blood pressure of the subject.

26. The method of claim 1, wherein the location and the one or more ultrasound parameters are selected to treat a condition of the subject, the condition comprising at least one of chronic pain, Parkinson's disease, depression, obsessive-compulsive disorder (OCD), obesity, epilepsy, schizophrenia, brain tumor, and essential tremor.

27. The method of claim 26, wherein the location is within a region in the brain that corresponds to the condition.

28. The method of claim 26, wherein the subject is experiencing one or more symptoms associated with the condition.

29. The method of claim 28, further comprising increasing the acoustic pressure to relieve the one or more symptoms.

30. The method of claim 28, wherein the focused ultrasound is provided as a burst having a pulse repetition frequency and a duty cycle, and the duty cycle is selected based on the one or more symptoms.

31. The system of claim 21, further comprising at least one camera for measuring the physical response of the subject.

32. The system of claim 31, wherein the at least one camera comprises a monochrome camera for recording at least one of an eye movement and pupil dilation.

33. The system of claim 31, wherein the at least one camera comprises a digital camera for recording a body movement.

34. The system of claim 21, wherein the ultrasound source is configured as a wearable device.

35. The system of claim 34, wherein the wearable device includes one or more securing features for aligning the ultrasound source with respect to the location in the brain of the subject.

36. The system of claim 35, wherein the one or more securing features are configured to secure the ultrasound source with respect to the location in the brain of the subject while the subject moves around.

37. The system of claim 34, wherein the wearable device is adapted for use to treat a condition of the subject, the condition comprising at least one of Parkinson's disease, essential tremor, chronic pain, and brain tumor.

38. The system of claim 37, wherein the ultrasound source is configured to permit a user to adjust at least one of the one or more ultrasound parameters.

39. The system of claim 38, wherein the user can adjust at least one of the one or more ultrasound parameters to correspond to one or more symptoms of the condition.

40. The system of claim 39, wherein the ultrasound source is configured to provide the focused ultrasound as a burst having a pulse repetition frequency and a duty cycle, and the user can adjust the duty cycle to correspond to the one or more symptoms.

41. The system of claim 40, wherein the user can adjust one or more of a function generator and an amplifier.

42. The system of claim 37, wherein the location is within a region in the brain that corresponds to the condition.

* * * * *

UNITED STATES PATENT AND TRADEMARK OFFICE
CERTIFICATE OF CORRECTION

PATENT NO. : 10,098,539 B2
APPLICATION NO. : 15/040926
DATED : October 16, 2018
INVENTOR(S) : Elisa E. Konofagou and Hermes Aryotto Salles Kamimura It is certified that error appears in the above-identified patent and that said Letters Patent is hereby corrected as shown below:

In the Specification

On Column 1, Line 15, please replace the Statement Regarding Federally Sponsored Research as follows:
This invention was made with government support under grants EB009041 and AG038961 awarded by the National Institutes of Health and by HR0011-15-2-0054 awarded by DOD/DARPA. The government has certain rights in the invention.

Signed and Sealed this
Twenty-second Day of September, 2020

Andrei Iancu
*Director of the United States Patent and Trademark Office*